United States Patent [19]  [11] Patent Number: 4,904,675
Winter-Mihaly et al.  [45] Date of Patent: Feb. 27, 1990

[54] PHAMACOLOGICALLY ACTIVE 5-CARBOXY-2-(5-TETRAZOLYL) PYRIDINES

[75] Inventors: Eva Winter-Mihaly, Bernex/Geneva; Christian Borel, La Plaine/Geneva; André J. Weith, Signy, all of Switzerland

[73] Assignee: Zyma SA, Nyon, Switzerland

[21] Appl. No.: 154,217

[22] Filed: Feb. 10, 1988

[30] Foreign Application Priority Data

Feb. 10, 1987 [GB] United Kingdom ................ 8702890

[51] Int. Cl.⁴ .................... A61K 31/455; C07D 401/04
[52] U.S. Cl. ................................ 514/340; 514/227.5; 514/236.2; 514/241; 514/252; 514/256; 514/307; 514/314; 514/318; 514/337; 514/338; 514/339; 514/333; 544/58.6; 544/124; 544/180; 544/238; 544/333; 544/360; 546/147; 546/174; 546/256; 546/269; 546/270; 546/271; 546/273; 546/274; 546/276; 546/277; 546/278; 546/279
[58] Field of Search ...................... 544/58.6, 124, 180, 544/238, 333, 360; 546/147, 174, 256, 269, 270, 271, 273, 274, 276, 277, 278, 279; 514/227.5, 236.2, 241, 252, 256, 307, 314, 333, 318, 337, 338, 339, 340

[56] References Cited

U.S. PATENT DOCUMENTS 3,501,486  3/1970  Ash et al. ............................ 260/296
4,404,012  9/1983  Orwick ................................... 71/92
4,717,727  1/1988  Gunzler et al. ...................... 514/354

FOREIGN PATENT DOCUMENTS 0041623  12/1981  European Pat. Off. .
0041624  12/1981  European Pat. Off. .
3432094   3/1986  Fed. Rep. of Germany .
2174395  11/1986  United Kingdom .

OTHER PUBLICATIONS

Majamaa et al., Eur. J. Biochem., 138, 239-245 (1984).
Tsukamoto et al., J. Med. Chem., 23, 734-738 (1980).
Ott et al., J. AM. Chem. Soc., 79, 5448-5454 (1957).
Daniher et al., J. Org. Chem., 31, 2709-2710 (1966).
Markovac et al., J. Org. Chem. 35, No. 3 841-843 (1970).
Prostakov et al., Chem. Abstr., 4, 22637C(1960).
Prostakov et al., Chem. Abstr., 55, 9398c(1961).
Prostakov et al., Chem. Abstr. 57, 12426i(1962).
Prostakov et al., Chem. Abstr. 64, 3464g(1966).
Kusakov et al., Chem. Abstr. 68, 7825k(1968).
Isagawa et al., Chem. Abstr. 68, 6884oh(1968).
Prostakov et al., Chem. Abstr. 70, 77725t(1969).
Markovac et al., Chem. Abstr., 72, 100447f(1970).
Prostakov et al., Chem. Abstr. 73, 12046m(1970).
Prostakov et al., Chem. Abstr. 78, 71879g(1973).
Prostakov et al., Chem. Abstr. 78, 136010w(1973).
Prostakov et al., Chem. Abstr. 84, 179989p(1976).
Grases et al., Chem. Abstr. 103, 133948g(1985).
Cardenas et al., Chem. Abstr. 105, 71674v(1986).

Primary Examiner—Mary C. Lee
Assistant Examiner—Beranrd I. Dentz
Attorney, Agent, or Firm—Wenderoth, Lind & Ponack

[57] ABSTRACT

Compounds of the formula I

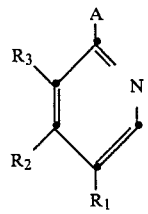

(I)

wherein the groups A, $R_1$, $R_2$ and $R_3$ are as defined in the specification, exhibit valuable pharmacological properties, especially as antifibrotic agents. They are prepared by methods known per se.

12 Claims, No Drawings

PHARMACOLOGICALLY ACTIVE 5-CARBOXY-2-(5-TETRAZOLYL) PYRIDINES

The present invention relates to compounds of the formula I

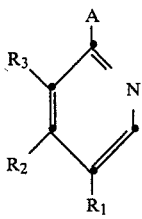

wherein
A represents carbamoyl, N-lower alkylcarbamoyl, N,N-di-lower alkylcarbamoyl, N-hydroxycarbamoyl in free or protected form, N-($C_1$–$C_{20}$)alkoxy-N-($C_1$–$C_{20}$)alkylcarbamoyl, the radical —C(=N—OH)—$NH_2$, the amidino radical —C(=NH)—$NH_2$, the N-lower alkylamidino radical —C(=NH)—NH(lower alkyl), the radical —C(=NH)—O(lower alkyl), 1-($C_1$–$C_{15}$-alkoxycarbonyl)-1-(lower alkoxy)-methoxycarbonyl, $C_3$–$C_7$-alkanoyl, 1-(N-hydroxyimino)-lower alkyl, 4,5-dihydro-2-(thia, oxa, imida)zolyl, 2-(thia, oxa)zolyl, 1-lower alkyl-4,5-dihydro-2-imidazolyl, imidazolyl, 1-acyl-imidazolyl, 2-benz-(othia, oxa, imida)zolyl, 1-acyl-2-benzimidazolyl, 5-tetrazolyl in free or protected from; or A represents carboxy or a pharmaceutically acceptable ester group thereof provided that $R_2$ is other than hydrogen, phenyl, nitro-phenyl, carboxy-phenyl and $C_1$–$C_2$-alkoxycarbonyl-phenyl;
$R_1$ represents carboxy or a pharmaceutically acceptable ester group thereof, and
$R_2$ represents hydrogen or a radical of the group comprising lower alkyl, cycloalkyl, aryl-lower alkyl, heteroaryl-lower alkyl and aryl each of which can be unsubstituted or substituted; and $R_3$ represents hydrogen; or
$R_2$ and $R_3$ together represent

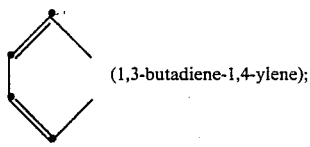

(1,3-butadiene-1,4-ylene);
with the proviso that $R_2$ is other than hydrogen, if
A represents N-hydroxycarbamoyl and $R_1$ is methoxycarbonyl, or
A represents N-hydroxyiminomethyl and $R_1$ is methoxycarbonyl or ethoxycarbonyl; or
A is 2-benzimidazolyl and $R_1$ is ethoxycarbonyl; and with the proviso that $R_2$ is other than phenyl, if
A is carbamoyl and $R_1$ is methoxycarbonyl or ethoxycarbonyl; tautomers and salts thereof, a process for the manufacture of these compounds, pharmaceutical compositions comprising said compounds, and their use for the manufacture of pharmaceutical preparations or as pharmacologically active compounds.

The general definitions used herein have the following meanings within the scope of the present invention.

The term "lower" means that groups so defined have preferably up to and including 7, especially up to and including 4, carbon atoms.

The radical —C(=N—OH)—$NH_2$ may be named hydroxyimino-carbamoyl. The radical —C(=N—H)—O(lower alkyl) may be named imino-lower alkoxycarbonyl.

Alkyl is preferably $C_1$–$C_{20}$-alkyl, such as hexadecyl or lower alkyl as defined below.

Lower alkyl is e.g. n-propyl, isopropyl, n-butyl, isobutyl, sec-butyl, tert-butyl, n-pentyl, isopentyl, neopentyl, n-hexyl, isohexyl or n-heptyl, preferably ethyl and especially methyl.

Imidazolyl represents e.g. 2- or 4(5)-imidazolyl. 1-Acyl-imidazolyl is preferably 1-acyl-2- or 1-acyl-4-imidazolyl.

Acyl is preferably lower alkanoyl, but may be also e.g. optionally substituted benzoyl or optionally substituted phenyl-lower alkoxycarbonyl, such as benzyloxycarbonyl. The optional substituents of benzoyl or phenyl-lower alkoxycarbonyl are the same as those mentioned below for aryl radicals.

$C_3$–$C_7$-alkanoyl is e.g. propionyl, n-butyryl, pivaloyl or valeroyl. Lower alkanoyl, is addition, comprises formyl and acetyl. 1-(N-Hydroxyimino)-lower alkyl represents the oximes of said lower alkanoyl groups of the formula —C(=N—OH)—(H or $C_1$–$C_6$-alkyl) and is e.g. N-hydroxyiminomethyl or 1-(N-hydroxyimino)-ethyl, -propyl or -butyl.

A pharmaceutically acceptable ester group of carboxy is advantageously an ester that may be convertible by solvolysis or under physiological conditions to the free carboxylic acid, e.g. $C_1$–$C_{20}$-alkoxycarbonyl, preferably lower alkoxycarbonyl; (amino, mono- or di-lower alkylamino)-substituted lower alkoxycarbonyl; carboxy-substituted lower alkoxycarbonyl, e.g. α-carboxy-substituted lower alkoxycarbonyl; lower alkoxycarbonyl-substituted lower alkoxycarbonyl, e.g. α-lower alkoxycarbonyl-substituted lower alkoxycarbonyl; aryl-substituted lower alkoxycarbonyl, e.g. optionally (halogen, lower alkyl or lower alkoxy)-substituted benzyloxycarbonyl or pyridylmethoxycarbonyl; (hydroxy, lower alkanoyloxy or lower alkoxy)-substituted lower alkoxycarbonyl, e.g. pivaloyloxymethoxycarbonyl; (hydroxy, lower alkanoyloxy or lower alkoxy)-substituted lower alkoxymethoxycarbonyl; 1-alkoxycarbonyl-1-lower alkoxymethoxycarbonyl, preferably 1-($C_1$–$C_{15}$-alkoxycarbonyl)-1-($C_1$–$C_7$-alkoxy)-methoxycarbonyl, especially 1-($C_1$–$C_{15}$-alkoxycarbonyl)-1-ethoxymethoxycarbonyl and in particular 1-ethoxycarbonyl-1-ethoxymethoxycarbonyl [cp. Synth. Commun. 16, 1431 (1986)]; 3-phthalidoxycarbonyl; (lower alkoxy, halogen)-substituted 3-phthalidoxycarbonyl, lower alkoxycarbonyloxy-lower alkoxycarbonyl, e.g. 1-(methoxy- or ethoxycarbonyloxy)-ethoxycarbonyl; aryloxycarbonyl, e.g. phenoxycarbonyl or phenoxycarbonyl advantageously substituted at the ortho position by carboxy or lower alkoxycarbonyl. Preferred as pharmaceutically acceptable ester groups are 1-($C_1$–$C_{15}$-alkoxycarbonyl-1-($C_1$–$C_7$-alkoxy)-methoxycarbonyl and $C_1$–$C_{20}$-alkoxycarbonyl, and especially lower alkoxycarbonyl.

5-Tetrazolyl can be protected e.g. analogously to the carboxy group. All the radicals ("R") used for esterification of carboxy in order to obtain a pharmaceutically acceptable ester group of carboxy as mentioned above may be likewise used to protect the NH group of 5-tetrazolyl. Thus, the pharmaceutically acceptable ester groups of carboxy mentioned above, —COOR, directly correspond to 5-tetrazolyl in protected form,

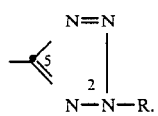

In addition, 5-tetrazolyl may be protected by acyl groups as defined above. Preferred as 5-tetrazolyl in protected form are 2-[1-($C_1$-$C_{15}$-alkoxycarbonyl)-1-lower alkoxy-methyl]-5-tetrazolyl and 2-lower alkanoyl-5-tetrazolyl.

N-hydroxycarbamoyl in protected form means e.g. mono- or diacylated or mono- or di-lower alkylated N-hydroxycarbamoyl. In case of monoacylation or -alkylation, normally the OH group is acylated. If a second acyl or alkyl group is introduced, the NH group will be acylated or alkylated too. N-hydroxycarbamoyl in protected form is preferably O-lower alkanoyl-N-hydroxycarbamoyl, N,O-di-lower alkanoyl-N-hydroxycarbamoyl, O-lower alkyl-N-hydroxycarbamoyl or N,O-di-lower alkyl-N-hydroxycarbamoyl.

Cycloalkyl has e.g. from 3 to 8, preferably from 5 to 7, ring carbon atoms and is e.g. cyclopropyl, cyclopentyl or cyclohexyl.

Aryl is a mono-, bi or polycarbocyclic aromatic radical, e.g. naphthyl, preferably phenyl.

Heteroaryl is a mono-, bi- or polycyclic aromatic radical containing at least one ring hetero atom, preferably of the group comprising nitrogen, oxygen and sulfur. Preferred are monocyclic heterocyclic radicals, and also monocyclic heterocyclic radicals having preferably one fused-on carbocyclic ring, especially benzo ring. Each heterocyclic ring consists of e.g. 3 to 7, preferably 5 and 6, ring members and may contain as ring members e.g. up to 4 identical or different hetero atoms. Preferred as 5-membered heteroaryl radicals are monoaza-, diaza-, triaza-, tetraza-, monoöxa-, monothia-, oxaza-, oxadiaza-, thiaza-and thiadiazacyclic radicals, such as pyrryl, pyrazolyl, imidazolyl, triazolyl, tetrazolyl, furyl, thienyl, isoxazolyl, oxazolyl, oxadiazolyl, isothiazolyl, thiazolyl or thiadiazolyl radicals, while 6-membered heteroaryl radicals are, for example corresponding monoaza-, diaza- or triaza-cyclic radicals, such as pyridyl, pyridazinyl, pyrimidinyl, pyrazinyl or triazinyl radicals. Monocyclic heterocyclic radicals having a fused-on benzo ring are e.g. indolyl, isoindolyl, benzimidazolyl, benzofuranyl, benzothienyl, benzothiazolyl, benzoxadiazolyl, benzothiadiazolyl, quinolinyl or isoquinolinyl radicals.

Lower alkyl, cycloalkyl, aryl and heteroaryl radicals are preferably unsubstituted, or may be substituted. As substituents, there come into consideration e.g. free, etherified or esterified hydroxy, such as hydroxy, lower alkoxy or lower alkanoyloxy; $C_3$-$C_{14}$-alkoxy wherein the alkyl chain is interrupted by 1 to 5 oxy groups; etherified mercapto, such as lower alkylthio; amino; secondary or tertiary amino, such as lower alkylamino, di-lower alkylamino, $C_4$-$C_6$-alkyleneamino, aza-, oxa- or thia-$C_3$-$C_5$-alkyleneamino, N-(lower alkyl or lower alkanoyl)-aza-$C_3$-$C_5$-alkyleneamino, or acylamino, preferably lower alkanoylamino; $C_3$-$C_{14}$-alkylamino wherein the alkyl chain is interrupted by 1 to 5 oxy and/or imino groups; halogen; free or functionally modified carboxyl, such as carboxy, lower alkoxycarbonyl, carbamoyl, N-mono- or N,N-di-lower alkylcarbamoyl or cyano; nitro; sulfo, lower alkoxysulfonyl or amidated sulfo, such as sulfamoyl, N-lower-alkyl-, N,N-di-lower-alkyl- or N-phenylsulfamoyl. Lower alkyl, in addition, may be substituted e.g. by cycloalkyl, aryl or heteroaryl. Furthermore, cycloalkyl may be substituted e.g. by lower alkyl, aryl or heteroaryl; and aryl and heteroaryl may be substituted also e.g. by lower alkyl, cycloalkyl or 1,2-methylenedioxy. Preferred substituents of lower alkyl are N-morpholino, N-piperazino, $C_3$-$C_{14}$-alkoxy wherein the alkyl chain is interrupted by 1 to 5 oxy groups and $C_3$-$C_{14}$-alkylamino wherein the alkyl chain is interrupted by 1 to 5 oxy and/or imino groups. Preferred substituents of cycloalkyl, aryl and heteroaryl are lower alkyl, hydroxy, lower alkoxy and halogen.

$C_3$-$C_{14}$-Alkoxy wherein the alkyl chain is interrupted by 1 to 5 oxy groups is e.g. —O—$(CH_2CH_2O)_n$—($C_1$-$C_4$)alkyl [n=1-5], preferably —O—$(CH_2CH_2O)_n$—$CH_3$ and especially the latter mentioned radical with n=1 or n=2.

$C_3$-$C_{14}$-Alkylamino wherein the alkyl chain is interrupted by 1 to 5 oxy and/or imino groups is e.g. —NH—$(CH_2CH_2X)_n$—($C_1$-$C_4$)alkyl [n=1-5, X=O or NH], preferably —NH—$(CH_2CH_2X)_n$—$CH_3$ and especially the latter mentioned radical with n=1 or n=2.

Halogen is preferably fluoro or chloro, but may be also bromo or iodo.

Salts are preferably pharmaceutically acceptable salts, especially metal or ammonium salts of said compounds of formula I having a free carboxy group, more particularly alkali or alkaline earth metal salts, e.g., the sodium, potassium, magnesium or calcium salt; or advantageously easily crystallizing ammonium salts derived from ammonia or organic amines, such as mono-, di or tri-lower (alkyl, cycloalkyl or hydroxyalkyl)-amines, lower alkylenediamines or lower (hydroxyalkyl or aralkyl)-alkylammonium hydroxides, e.g., methylamine, diethylamine, triethylamine, dicyclohexylamine, triethanolamine, ethylenediamine, tris-(hydroxymethyl)aminomethane, N-methyl-D-glucamine or benzyltrimethylammonium hydroxide. Said compounds of formula I having a basic group form acid addition salts of preferably the pharmaceutically acceptable inorganic or organic acids, such as of strong mineral acids, aliphatic or aromatic carboxylic or sulfonic acids, e.g. hydrochloric, succinic, salicylic, methanesulfonic or p-toluenesulfonic acid.

It is also possible to use pharmaceutically unacceptable salts for isolation or purification. Only pharmaceutically acceptable, non-toxic salts are used therapeutically and are therefore preferred.

The compounds of this invention exhibit valuable pharmacological properties, e.g. they are inhibitors of collagen prolinehydroxylase and decrease collagen synthesis; they are therefore useful e.g. as antifibrotic agents for the treatment and prophylaxis of disorders such as hepatic fibrosis and cirrhosis, pulmonary fibrosis, nephrosclerosis, arteriosclerosis, scleroderma myelofibrosis, chronic arthritis, rheumatoid arthritis, hypertrophic scar formation, osteoarthritis or keloids.

Prolyl-4-hydroxylase activity measurement: Prolyl-4-hydroxylase can be isolated from an ammonium sulfate fraction of chick embryo, according to the method of I. Tuderman et al. [Eur. J. Biochem. 52, 9–16 (1975)]. Prolyl-4-hydroxylase activity can be e.g. determined in vitro by the method based on the decarboxylation of 2-oxo-1-$^{14}$C-glutarate according to K. I. Kivirikko et al., Methods in Enzymology 82A, 245–304 (1982), $IC_{50}$ values (drug concentration which induces a 50% decrease of the enzymatic reaction) are determined for the compounds of the invention, which amount to about 0.5 $\mu$M or above.

Collagen production in vitro: The effect of a compound of the formula I on collagen synthesis can be studied in vitro e.g. in egg embryo fibroblast cultures according to M. Duchene et al., FEBS Letter 135, 119–122 (1981). After 24 hours of drug incubation, collagen type I secreted in medium can be measured by radioimmunoassay (e.g. with a kit from the Centre de Radioanalyse, Institut Pasteur, Lyon, France). Inhibition (in %) of synthetized type I collagen induced by the tested compound can be calculated.

Preferred are said compounds of the formula I, wherein $R_2$ represents hydrogen or a radical of the group comprising lower alkyl, cycloalkyl, aryl-lower alkyl, heteroaryl-lower alkyl and aryl each of which can be unsubstituted or substituted by amino, lower alkylamino, di-lower alkylamino, N-piperidino, N-morpholino, N-thiomorpholino, N-piperazino, 4-(lower alkyl or lower alkanoyl)-N-piperazino, lower alkoxy, $C_3$–$C_{14}$-alkoxy wherein the alkyl chain is interrupted by 1 to 5 oxy groups, or $C_3$–$C_{14}$-alkylamino wherein the alkyl chain is interrupted by 1 to 5 oxy and/or imino groups; and $R_3$ represents hydrogen; or $R_2$ and $R_3$ together represent 1,3-butadiene-1,4-ylene.

A preferred embodiment of the invention are the compounds of the formula I, wherein A represents N-lower alkylcarbamoyl, N,N-di-lower alkylcarbamoyl, N-hydroxycarbamoyl, N-($C_1$–$C_{20}$)alkoxy-N-($C_1$–$C_{20}$)-alkylcarbamoyl, the radical —C(=N—OH)—NH$_2$, the N-lower alkylamidino radical —C(=N—H)—NH(lower alkyl), the radical —C(=NH)—O(-lower alkyl), 1-lower alkoxycarbonyl-1-lower alkoxycarbonyl-1-lower alkoxy-methoxycarbonyl, $C_3$–$C_7$-alkanoyl, 1-(N-hydroxyimino)-lower alkyl, 4,5-dihydro-2-(thia, oxa, imida)zolyl, 2-(thia, imida)zolyl, 1-lower alkyl-4,5-dihydro-2-imidazolyl, 2-benzothiazolyl, 5-tetrazolyl, 2-lower alkanoyl-5-tetrazolyl or 2-(1-lower alkoxycarbonyl-1-lower alkoxy-methyl)-5-tetrazolyl; or A represents carboxy or $C_1$–$C_{20}$-alkoxycarbonyl provided that $R_2$ in other than hydrogen and unsubstituted phenyl;

$R_1$ represents carboxy, $C_1$–$C_{20}$-alkoxycarbonyl or 1-lower alkoxycarbonyl-1-lower alkoxy-methoxycarbonyl, and $R_2$ represents hydrogen, lower alkyl, $C_5$–$C_7$-cycloalkyl, phenyl-lower alkyl or phenyl, whereby in the latter two radicals phenyl is unsubstituted or substituted by lower alkyl, hydroxy, lower alkoxy and/or halogen, with the proviso that $R_2$ is other than hydrogen, if A represents N-hydroxycarbamoyl and $R_1$ is methoxycarbonyl; and $R_3$ represents hydrogen; or $R_2$ and $R_3$ together represent 1,3-butadiene-1,4-ylene; tautomers and pharmaceutically acceptable salts thereof.

Another preferred embodiment of the invention are the compounds of the formula I, wherein A represents N-hydroxycarbamoyl, N-($C_1$–$C_{20}$)-alkoxy-N-($C_1$–$C_{20}$) alkylcarbamoyl, the radical —C(=N—OH)-NH$_2$, the N-lower alkylamidino radical —C(=NH)—NH(lower alkyl), the radical —C(=NH)—O(lower alkyl), 1-lower alkoxycarbonyl-1-lower alkoxymethoxycarbonyl, $C_3$–$C_7$-alkanoyl, 1-(N-hydroxyimino)-lower alkyl, 4,5-dihydro-2-(thia, oxa, imida)zolyl, 2-(thia, imida)zolyl, 1-lower alkyl-4,5-dihydro-2-imidazolyl, 2-benzothiazolyl, 5-tetrazolyl, 2-lower alkanoyl-5-tetrazolyl or 2-(1-lower alkoxycarbonyl-1-lower alkoxy-methyl)-5-tetrazolyl; or A represents carboxy or $C_1$–$C_{20}$-alkoxycarbonyl provided that $R_2$ in other than hydrogen and phenyl;

$R_1$ represents carboxy, $C_1$–$C_{20}$-alkoxycarbonyl or 1-lower alkoxycarbonyl-1-lower alkoxy-methoxycarbonyl, and $R_2$ represents hydrogen, lower alkyl, $C_5$–$C_7$-cycloalkyl or phenyl, with the proviso that $R_2$ is other than hydrogen, if A represents N-hydroxycarbamoyl and $R_1$ is methoxycarbonyl; and $R_3$ represents hydrogen; or $R_2$ and $R_3$ together represent 1,3-butadiene-1,4-ylene; tautomers and pharmaceutically acceptable salts thereof.

In particular preferred are the compounds of the formula I, wherein A represents N-hydroxycarbamoyl in free or protected form, 5-tetrazolyl in free or protected form or carboxy or a pharmaceutically acceptable ester group thereof, $R_1$ represents carboxy or a pharmaceutically acceptable ester group thereof, $R_2$ and $R_3$ represent hydrogen, or $R_2$ and $R_3$ together represent 1,3-butadiene-1,4-ylene; with the proviso that $R_2$ and $R_3$ must be together 1,3-butadiene-1,4-ylene, if A is N-hydroxycarbamoyl and $R_1$ is methoxycarbonyl, or if A is carboxy or lower alkoxycarbonyl; and pharmaceutically acceptable salts thereof.

Further preferred are compounds of formula I, wherein A represents N-lower alkylcarbamoyl, N,N-di-lower alkylcarbamoyl, N-hydroxycarbamoyl, the radical —C(=N—OH)—NH$_2$, the N-lower alkylamidino radical —C(=NH)—NH(lower alkyl), the radical —(=NH)—O(lower alkyl), $C_3$–$C_7$-alkanoyl, 1-(N-hydroxyimino)-$C_2$–$C_7$-alkyl, 4,5-dihydro-2-thiazolyl, 2-thiazolyl, 4,5-dihydro-2-imidazolyl, 1-lower alkyl-4,5-dihydro-2-imidazolyl, 2-imidazolyl, 4,5-dihydro-2-oxazolyl, 2-benzothiazolyl or 5-tetrazolyl, $R_1$ represents carboxy or lower alkoxycarbonyl, $R_2$ is hydrogen, lower alkyl, cycloalkyl, phenyllower alkyl or phenyl, whereby in the latter two radicals phenyl is unsubstituted or substituted by lower alkyl, hydroxy, lower alkoxy and/or halogen, with the proviso that $R_2$ is other than hydrogen, if A represents N-hydroxycarbamoyl and $R_1$ is methoxycarbonyl; and $R_3$ represents hydrogen; or $R_2$ and $R_3$ together represent 1,3-butadiene-1,4-ylene; tautomers and pharmaceutically acceptable salts thereof.

Especially preferred are the compounds of formula I, wherein A represents N-hydroxycarbamoyl, 5-tetrazolyl or carboxy, $R_1$ is carboxy or lower alkoxycarbonyl, $R_2$ is hydrogen or lower alkyl but must be lower alkyl, if A is N-hydroxycarbamoyl and $R_1$ is methoxycarbonyl, or if A is carboxy; and $R_3$ represents hydrogen; and pharmaceutically acceptable salts thereof.

Above all are preferred the compounds of formula I described in the examples and pharmaceutically acceptable salts thereof.

The compounds of the formula I can be produced by processes known per se, e.g. by reacting a compound of formula II

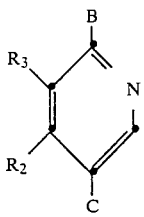 (II)

wherein B is a radical capable of being transformed into a group A, or is a group A as defined under formula I, C is a radical capable of being transformed into a group $R_1$, or is a group $R_1$ as defined under formula I, with the proviso that at least one of the groups B and C is other than the groups A and $R_1$ of formula I, and $R_2$ and $R_3$ are as defined under formula I, with a reagent forming the group A and/or $R_1$; and/or, if desired, converting a resulting compound of formula I into another compound of formula I, and/or converting a resulting salt into the free compound or into an other salt, and/or converting a resulting free compound of the formula I having salt-forming properties into a salt, and/or separating a resulting mixture of stereoisomers or optical isomers, such as a diastereoisomeric mixture, into the individual stereoisomers, optical isomers or enantiomeric mixtures, respectively, and/or splitting enantiomeric mixtures, such as a racemate, into the optical isomers.

A group B which is capable of being transformed into a group A is preferably free of functionally modified carboxy, also e.g. free or functionally modified formyl. Functionally modified carboxy is e.g. cyano, esterified carboxy, such as lower alkoxycarbonyl, halocarbonyl, such as chlorocarbonyl (—COCl), the anhydride or a mixed anhydride e.g. derived from a lower alkoxycarbonyl halide, such as ethyl chloroformate, or from a hindered lower alkanoyl halide, e.g. pivaloyl chloride. In many cases it is advantageous first to convert cyano to imino-lower alkoxycarbonyl, e.g. by reaction with an alkalimetal alcoholate, such as sodium methoxide or ethoxide [cp. Chem. Rev. 61, 179 (1961)]. Imino-lower alkoxycarbonyl normally is more reactive than cyano and can be prepared either in situ or can be isolated before, if necessary, being subjected to one of the conversions leading to other groups A as mentioned below.

A group C which is capable of being transformed into a group $R_1$ is preferably functionally modified carboxy, such as cyano, halocarbonyl or a mixed anhydride with carboxy as defined above. Furthermore, there come into consideration e.g. halogen, methyl, hydroxymethyl, etherified or esterified hydroxymethyl, halogenmethyl, free or functionally modified formyl or lower alkanoyl.

Examples for suitable reagents forming the group A and/or $R_1$ can be found below, where some of the possible conversions B→A and C→$R_1$ are described.

Compounds of formula I, wherein A represents carbamoyl, N-lower alkylcarbamoyl or N,N-di-lower alkylcarbamoyl, can be prepared e.g. by reacting a corresponding compound of either formula II or I, wherein B(A) represents carboxy, functionally modified carboxy or lower alkoxycarbonyl, with ammonia, a mono- or di-lower alkylamine respectively.

Furthermore, compounds of formula I, whether A represents carbamoyl, can be prepared e.g. from a corresponding compound of formula II, wherein B is cyano, e.g. by careful hydrolysis, e.g. with 96% sulfuric acid, or by treatment with an alkalimetal hydroxide, e.g. dilute aqueous NaOH, and hydrogen peroxide.

Compounds of formula I(II), wherein A(B) and/or $R_1$ represent(s) (lower) alkoxycarbonyl or substituted (lower) alkoxycarbonyl, i.e. esterified carboxy, can also be prepared e.g. by reacting a compound of formula II, wherein B and/or $R_1$ represent(s) cyano with an optionally substituted (lower) alkanol followed by careful hydrolysis with water.

Compounds of formula I, wherein A represents hydroxyimino-carbamoyl, can be prepared e.g. by reacting a corresponding compound of either formula II or I, wherein B(A) represents cyano or imino-lower alkoxycarbonyl, with hydroxylamine or a salt, e.g. the hydrochloride or the sulfate, thereof.

Compounds of formula I, wherein A represents amidino or N-lower alkylamidino, can be prepared e.g. by reacting a corresponding compound of either formula II or I, wherein B(A) represents cyano or imino-lower alkoxycarbonyl, with ammonia or a lower alkylamine respectively.

Compounds of formula I, wherein A represents 4,5-dihydro-2-thiazolyl, 4,5-dihydro-2-oxazolyl, 4,5-dihydro-2-imidazolyl, 1-lower alkyl-4,5-dihydro-2-imidazolyl, 2-benzothiazolyl, 2-benzoxazolyl or 2-benzimidazolyl, can be generally prepared e.g. by reacting a corresponding compound of either formula II or I, wherein B(A) represents carboxy or preferably functionally modified carboxy as defined above, especially cyano or imino-lower alkoxycarbonyl, with 2-aminoethanethiol, 2aminoethanol, 1,2-diaminoethane, 1-(lower alkylamino)-2-aminoethane, 2-aminoethiophenol, 2-aminophenol or 1,2-diaminobenzene respectively [cp. Chem. Rev. 61, 179–211 (1960) or Rodd's Chemistry of Carbon Compounds, Vol. IVc, M. F. Ansell (Ed.), Elsevier, Amsterdam et al. 1986, pp. 156–158, 197–200, 317–320, 347–348, 429 and 456].

Compounds of formula I wherein A represents 5-tetrazolyl can be prepared e.g. by condensing a compound of formula II, wherein B represents e.g. cyano, or cyano activated e.g. in the form of imino-lower alkoxycarbonyl as described above, with hydrazoic acid or a compound which serves as a source of hydrazoic acid, e.g. a metal or ammonium salt of hydrazoic acid, preferably an alkali metal azide such as sodium azide or ammonium azide. Said condensation is carried out according to methods known per se, e.g. as described in Barton et al., Comprehensive Organic Chemistry Vol. 4, pp. 407–409 (1979), preferably in the presence of an acid, e.g. hydrochloric acid or ammonium chloride [cp. also Synthesis 1973, 80 and J. Amer. Chem. Soc. 80, 3908 (1958)].

Compounds of formula I, wherein A represents N-hydroxycarbamoyl, can be prepared e.g. by reacting a corresponding compound of either formula II or I, wherein B(A) represents carboxy, functionally modified carboxy as defined above or lower alkoxycarbonyl, with hydroxylamine or a salt thereof. As an example, lower alkoxycarbonyl can be treated with hydroxylamine under basic conditions [cp. J. Med. Chem. 22, 589 (1979)].

Compounds of formula I, wherein A represents N-($C_1$-$C_{20}$)alkoxy-N-($C_1$-$C_{20}$)alkylcarbamoyl, can be prepared e.g. by reacting e.g. by reacting another compound of formula I, wherein A represents N-hydroxycarbamoyl, with a $C_1$-$C_{20}$-alkanol e.g. in the presence of an acid, such as sulfuric acid.

Compounds of formula I, wherein A represents 2-thiazolyl, 2-oxazolyl, 2-imidazolyl or 1-acyl-2-imidazolyl, can be prepared e.g. by oxidizing a corresponding compound of either formula II or I, wherein B(A) represents 4,5-dihydro-2-thiazolyl, 4,5-dihydro-2-oxazolyl, 4,5-dihydro-2-imidazolyl or 1-acyl-4,5-dihydro-2-imidazolyl respectively [cp. e.g. J. Amer. Chem. Soc. 96, 2463 (1974)].

Compounds of formula I, wherein A represents 4(5)-imidazolyl, can be prepared e.g. by reacting a corresponding compound of formula II, wherein B is acetyl, with a lower alkyl methanimidate, e.g. $HC(=NH)OC_2H_5$, in the presence of ammonia [cp. Arch. Pharm. 307, 972 (1974)].

Compounds either of formula II or I, wherein B(A) represents lower alkanoyl, can be prepared e.g. by reacting a compound of formula II, wherein B is preferably cyano, with preferably a Grignard compound of the formula $C_1-C_6$-alkyl-Mg-Hal [Hal=Halogen]. After acidic hydrolysis the desired keto compound is obtained.

Compounds of formula I, wherein A represents 1-(N-hydroxyimino)-lower alkyl, can be prepared e.g. by reacting a corresponding compound of either formula II or I, wherein B(A) represents formyl or $C_2-C_7$-alkanoyl, with hydroxylamine or a salt thereof.

Compounds of formula I, wherein A represents 1-acyl-(2 to 4)-imidazolyl, 1-acyl-2-benzimidazolyl, 2-acyl-5-tetrazolyl, O-acyl- or N,O-diacyl-N-hydroxycarbamoyl, can be prepared e.g. by reacting another compound of formula I, wherein A represents [2 or 4(5)]-imidazolyl, 2-benzimidazolyl, 5-tetrazolyl or N-hydroxycarbamoyl, with an appropriate acylating agent introducing the desired acyl group(s), e.g. an acid halide, anhydride or mixed anhydride as mentioned above.

Acylating agents that come into consideration for acylating 5-tetrazolyl are e.g. acid chlorides of the formula $Cl-C(=O)-X$ [X≙lower alkyl, aryl, O(lower alkyl), O(aryl)], isocyanates, e.g. phenylisocyanate, keten dimer or cyanogen bromide. Normally, 5-tetrazolyl is acylated (as well as alkylated) in the 2-position.

Acylating agents that come into consideration for acylating hydroxamic acids (=N-hydroxycarbamoyl) are e.g. acid chlorides, acid anhydrides, isocyanates, keten dimer or di-lower alkylacetals.

O-Monoalkylation of N-hydroxycarbamoyl is e.g. carried out by treatment with a lower alkyl halide in the presence of a base, e.g. sodium methoxide. Dialkylation of N-hydroxycarbamoyl can be accomplished e.g. by reaction of its potassium salt with a lower alkyl halide.

Compounds of formula I, wherein $R_1$ (and/or A) is a pharmaceutically acceptable ester group, are e.g. prepared by reacting a compound of formula I, wherein $R_1$ (and/or A) represents carboxy, or a compound of formula II, wherein C represents functionally modified carboxy and B is a group A as defined for formula I (or is functionally modified carboxy), with the corresponding alcohol.

The esterification of free carboxy groups advantageously takes place in the presence of an acidic water-removing catalyst, such as a protonic acid, e.g. sulfuric acid, or a Lewis acid, e.g. boron trifluoride etherate, in an excess of the alcohol used and/or in an inert solvent, if necessary with the removal by e.g. azeotropic distillation of the water freed during the reaction. The reaction can also be carried out in the presence of water-binding condensation agents, such as suitably substituted carbodiimides, e.g. N,N'-dicyclohexyl carbodiimide, optionally in inert organic solvents. Functionally modified carboxy, e.g. mixed anhydrides or acid halides, are reacted e.g. in the presence of acid-binding agents, for example organic bases, especially tertiary nitrogen bases, such as triethylamine, ethyldiisopropylamine or pyridine, or also inorganic bases, for example alkali metal or alkaline earth metal hydroxides or carbonates, such as sodium, potassium or calcium hydroxide or carbonate, with alcohols or with alcoholates, for example alkali metal lower alkoxides.

Furthermore, the compounds of formula I, wherein $R_1$ (and/or A) is a pharmaceutically acceptable ester group, can be prepared e.g. by condensing another compound of formula I, wherein $R_1$ (and/or A) represents carboxy, with an esterifying agent of the formula III

$$R_4-Z \qquad (III)$$

wherein Z represents hydroxy or a reactive esterified hydroxy group, and $R_4$ represents any of the ester radicals defined hereinabove.

A reactive esterified hydroxy group Z in a compound of the formula III is a hydroxy group esterified by a strong inorganic or organic acid. Corresponding Z groups are in particular halogen, for example chlorine, bromine or preferably iodine, also sulfonyloxy groups, such as lower alkyl- or arylsulfonyloxy groups, for example methane-, ethane-, benzene-, or toluene-sulfonyloxy groups.

The esterification of the carboxy group $R_1$ (and/or A), optionally in salt form, in a compound of formula I, with a compound of formula III wherein Z represents a reactive esterified hydroxy group, is performed in a manner known per se, in the presence of e.g. an organic base, such as an organic amine, e.g. a tertiary amine, such as tri-lower alkylamine, e.g. trimethylamine, triethylamine or ethyl-di-isopropylamine, an N,N-di-lower-alkyl-aniline, e.g. N,N-dimethyl-aniline, a cyclic tertiary amine, such as an N-lower-alkylated morpholine, e.g. N-methyl-morpholine, a base of the pyridine type, e.g. pyridine, an inorganic base, e.g. hydroxides, carbonates, or hydrogen carbonates of alkali metals or alkaline-earth metals, e.g. sodium, potassium or calcium hydroxide, carbonate or hydrogen carbonate, or a quaternary ammonium base, such as a tetraalkylammonium hydroxide, carbonate or hydrogen carbonate, e.g. in which alkyl is methyl, ethyl, propyl, isopropyl, butyl, or the like.

The compound of the formula I, wherein $R_1$ (and/or A) is carboxy, is preferably first converted into a salt of one of the stated organic or inorganic bases, especially into the sodium or potassium salt, and is then reacted with a compound of the formula III. The compounds of formula III are known or can be prepared by methods well-known to the art.

A compound of the formula III wherein Z is a reactive esterified hydroxy group can be prepared in situ. For example, a compound of the formula III wherein Z is chloro can be converted by treatment with sodium iodide in a solvent, for example in acetone or acetonitrile, into a compound of the formula III wherein Z is iodo; or esterification can be carried out with a chloro compound of the formula III in the presence of sodium iodide.

The same reactions described above for the conversion of carboxy into pharmaceutically acceptable ester groups thereof may be applied for converting A=5-tetrazolyl into A=protected 5-tetrazolyl.

For example, compounds of formula I, wherein A represents 2-[1-($C_1$-$C_{15}$-alkoxycarbonyl)-1-lower alkoxy-methyl]-5-tetrazolyl, can be prepared by reacting another compound of formula I, wherein A represents 5-tetrazolyl, with a $C_1$-$C_{15}$-alkyl 2-halo-2-lower alkoxyacetate e.g. in the presence of a base, such as triethylamine.

Most of the starting materials are derivatives of the known 2,5-di-carboxy-pyridine. 5-Carboxy-2-cyano-pyridine, also with an additional substituent in 4- or 3,4-position, can be prepared e.g. from 3-formyl-pyridine or 3-carboxy-pyridine—each optionally substituted in 4- or 4,5-position—by (1) oxidation to the corresponding 3-carboxy-pyridine-N-oxide and (2) treating the latter inter alia with an alkalimetal cyanide, e.g. sodium or potassium cyanide, according to the Reissert-Henze method or some method related thereto [cp. Heterocycles 22, 2375 (1984)]. For example, cyanation of the substituted pyridine-N-oxides may be accomplished via the 1-methoxypyridinium ions by reacting them with trimethylsilylcyanide and dimethylcarbamoyl chloride [cp. Heterocycles 22, 93 (1984)].

The introduction of a substituent $R_2$, e.g. lower alkyl, cycloalkyl, aryl-lower alkyl, heteroaryl-lower alkyl or aryl, into the 4-position of 3-formyl-pyridine can be achieved e.g. as follows: (1) protecting the formyl group, e.g. as an 1,2-ethylenedioxy acetal; (2) treatment with chloroformic acid phenyl ester yielding a N-phenyloxycarbonyl-pyridinium salt; (3) reaction with $R_2$MgHal ($R_2$=substituent, Hal=halogen) yielding 4-$R_2$-1,4-dihydropyridine; (4) oxidation e.g. with sulfur, such as $S_8$, yielding the free 4-$R_2$-substituted pyridine (the N-phenyloxycarbonyl substituent is split off) and (5) deprotecting the formyl group e.g. by acidic hydrolysis yielding the desired 4-$R_2$-3-formyl-pyridine [cp. Heterocycles 22, 339 (1984)]. 3-(Carboxy or formyl)-pyridine substituted in 4,5-position by a benzo ring corresponds to the known 4-(carboxy or formyl)-isoquinoline.

3-Carboxy-pyridines substituted in 4-position by a group $R_2$ which is other than hydrogen can be also prepared e.g. by total synthesis of the pyridine ring in a manner known per se. For example, reacting a β-ketoacetic acid alkyl ester of the formula $R_2$COCH$_2$COOAlk with cyanoacetamide yields a 2,6-dihydroxy-4-$R_2$-3-cyanopyridine which can be converted to the corresponding 2,6-dichloro-4-$R_2$-3-cyanopyridine by reaction with a halogenating agent, e.g. POCl$_3$. In the latter, the two chloro substituents can be reduced to hydrogen e.g. with hydrogen in the presence of Pd (e.g. from PdCl$_3$), and the resulting 4-$R_2$-3-cyano-pyridine is saponified to yield the desired 4-$R_2$-3-carboxypyridine [cp. J. Org. Chem. 25, 560 (1960) or Tetrahedron 33, 113 b 1977)].

Compounds of the formula II, wherein B represents formyl and C is carboxy, are known to the art [cp. JP-A-77-42,883≙C. A. 87, 117786y (1977)]or can be prepared e.g. from a corresponding compound of formula II, wherein B is cyano, by selective reduction, e.g. with SnCl$_2$/HCl according to Org. Synth. Coll. Vol. 3, 626 (1955).

Conversion of a compound of formula I(II) wherein A(B) and/or $R_1$ represent(s) e.g. lower alkoxycarbonyl, cyano or otherwise functionally modified carboxy, to a compound of formula I wherein A and/or $R_1$ represent(s) carboxy is advantageously carried out by hydrolysis with inorganic acids such as hydrohalic or sulfuric acid or with aqueous alkalies, preferably alkali metal hydroxides such as lithium or sodium hydroxide.

If any intermediates mentioned contain interfering reactive groups, e.g. carboxy, hydroxy, amino or mercapto groups, such may advantageously be temporarily protected at any stage with easily removable protecting groups. The choice of protecting groups for a particular reaction depends on several factors, e.g. the nature of the functional group to be protected, the structure and stability of the molecule of which the substituent is the functional group, and the reaction conditions. Protecting groups that meet these conditions and their introduction and removal are known to the art and are described, for example, in J. F. W. McOmie, "Protective Groups in Organic Chemistry", Plenum Press, London, New York 1973.

Depending upon the reaction conditions, the compounds of formula I are either obtained in the free form, or as a salt thereof. Any resulting base can be converted into a corresponding acid addition salt, preferably with the use of a therapeutically useful acid or an anion exchange preparation, or resulting salts can be converted into the corresponding free bases, for example, with the use of a stronger base, such as a metal or ammonium hydroxide or a basic salt, e.g. an alkali metal hydroxide or carbonate, or a cation exchange preparation. On the other hand, compounds of formula I containing acidic groups, e.g. carboxy or a phenolic hydroxy group, can be converted into salts in a manner known per se by treating with a base, e.g. an alkali metal hydroxide or alkoxide, an alkali metal or alkaline-earth metal salt, e.g. sodium hydrogen carbonate, ammonia or a suitable organic amine. The free compounds can be obtained by treating such salts with an acid. In view of the close relationship between the free compounds and the compounds in the form of their salts, whenever a compound is referred to in this context, a corresponding salt is also intended, provided such is possible or appropriate under the circumstances.

Compounds of formula I containing at least one asymmetric carbon atom, can be found as R- or S-enantiomers as well as enantiomeric mixtures thereof, such as a racemate. The present invention is intended to include all these forms, also those further isomers, and mixtures of at least two isomers, for example a diastereoisomeric mixture or enantiomeric mixture, which become possible if one or more further asymmetric center(s) are present within the molecule.

Any resulting mixtures of diastereoisomers, mixtures of racemates or geometric isomers can be separated on the basis of the physicochemical differences of the constituents, in known manner, into single diastereoisomers, racemates, or geometric isomers, for example by chromatography and/or fractional crystallisation.

Any resulting enantiomeric mixtures, such as racemates can be resolved into the optical isomers (antipodes) by known methods, for example by recrystallisation from an optically active solvent, or with the aid of microorganisms, or by e.g. reacting an acidic end product with an optically active base that forms salts with the racemic acid, and separating the salts obtained in this manner, for example by fractional crystallization, into the diastereoisomeric salts from which the optically active carboxylic acid antipodes can be liberated on acidification.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, e.g. in a temperature range from $-20°$ C. to $+200°$ C., preferably at the boiling point of the solvents used, and at atmospheric or super-atmospheric pressure. The preferred solvents, catalysts and reaction conditions are set forth in the appended illustrative examples.

The compounds, including their salts, can also be obtained in the form of their hydrates, or include other solvents used for their crystallization.

The invention further includes any variant of the present processes, in which an intermediate product obtainable at any stage thereof is used as starting material and the remaining steps are carried out, or the process is discontinued at any stage thereof, or in which a starting material is formed under the reaction conditions, or in which a reaction component is used in the form of a salt or an optically pure antipode. Mainly those starting materials should be used in said reactions, that lead to the formation of those compounds indicated above as being especially useful. The invention also relates to novel starting materials and processes for their manufacture.

The pharmacologically acceptable compounds of the present invention can be used e.g. for the manufacture of pharmaceutical preparations that contain an effective amount of the active ingredient alone or together with inorganic or organic, solid or liquid, pharmaceutically acceptable carriers. The pharmaceutical preparations are e.g. for enteral, such as oral or rectal, topical (transdermal) and parenteral, such as intraperitoneal, intramuscular or intravenous, administration to warm-blooded animals including humans.

For oral administration there are used e.g. tablets or gelatine capsules that contain the active ingredient together with diluents, e.g. lactose, dextrose, sucrose, mannitol, sorbitol and/or cellulose, and lubricants, e.g. silica, talc, stearic acid or salts thereof, such as magnesium or calcium stearate, and/or polyethylene glycol; tablets also contain binders, e.g. starches, such as maize, wheat, rice or arrowroot starch, gelatine, tragacanth, methylcellulose, sodium carboxymethylcellulose and/or polyvinylpyrrolidone, and, if desired, disintegrators, e.g. starches, agar, alginic acid or a salt thereof, such as sodium alginate, and/or e.g. effervescent mixtures, adsorbents, colourings, flavourings or sweeteners.

For parenteral administration there are suitable especially infusion solutions, preferably isotonic aqueous solutions or suspensions, it being possible to prepare these before use, e.g. from lyophilised preparations that contain the active ingredient alone or together with a carrier, e.g. mannitol. Such preparations may be sterilised and/or contain adjuncts, for example preservatives, stabilisers, wetting agents and/or emulsifiers, solubilisers, salts for regulating the osmotic pressure and/or buffers.

For topical and transdermal administration preferably hydrogels, emulsions, such as creams and ointments, and microemulsions such as isotropic transparent emulsion gels are used. Such preparations contain the active ingredient together with e.g. preservatives, stabilizers, thickening agents, emulsifiers, oils, solubilizers and penetration enhancers.

The present pharmaceutical preparations, which, if desired, may contain other pharmacologically active substances, are manufactured in a manner known per se, e.g. by means of conventional mixing, granulating, tabletting, film coating, dissolving, confectioning or lyophilising processes, and contain from approximately 0.1 to 100%, especially from approximately 1 to approximately 50% or, in the case of lyophilisates, up to 100%, of the active ingredient.

Depending upon the type of disorder, the individual condition of the organism and the mode of administration, the daily dose to be administered for the treatment of a warm-blooded animal (human or animal) weighing approximately 70 kg is from approximately 5 mg to approximately 3 g, and especially from 50 mg to 1 g.

The following Examples (a) to (f) are intended to illustrate the manufacture of some typical forms of administration, but do not in any way represent the only embodiments of those forms of administration.

(a) 250 g of active substance are mixed with 550 g of lactose, 100 g of microcrystalline cellulose and 100 g of maize starch, and the mixture is moistened with an aqueous past of 10 g maize starch, and granulated by being passed through a sieve. After drying, 60 g of talc, 10 g of magnesium stearate and 20 g of colloidal silica are added and the mixture is pressed to form 10,000 tablets each weighing 119 mg and each containing 25 mg of active substance, which may, if desired, be provided with dividing notches for a finer adjustment of the dosage.

(b) A granulate is prepared from 100 g of active substance, 600 g of lactose, 300 g of cellulose, 200 g of maize starch and an aqueous past of 120 g of maize starch. After drying, it is mixed with 30 g of colloidal silica, 90 g of talc and 15 g of magnesium stearate and processed so as to form 10,000 film coating cores. These are subsequently coated with an aqueous suspension of 20 g low substituted hydroxypropylmethylcellulose, 15 g of talc and 10 g of titanium dioxide and dried. The resulting film coated tablets each weigh 150 mg and contain 10 mg of active substance.

(c) A sterile solution of 5.0 g of the active substance in 5000 ml of distilled water is introduced into 5 ml ampoules, the ampoules containing 5 mg of active ingredient in 5 ml of solution.

(d) 25 g of active substance and 1975 g of finely ground suppository base (for example, cocoa butter) are thoroughly mixed and then melted. 1000 suppositories of 2 g are cast from the melt which has been kept homogenous by stirring. They each contain 25 mg of active substance.

(e) 25 g of active substance and 120 g of granular lactose, e.g. Tablettose ®, 95 g of microcrystalline cellulose, e.g. Avicel ® PH-102, 7 g of colloidal silicagel and 3 g of magnesium stearate are intimately mixed. The resulting powder is then sieved and filled in 250 mg portions into 1,000 gelatine capsules.

(f) 400 g of active substances are dispersed in 24 l of distilled water with the addition of 70 g of a preservative, e.g. methylparaben, and 530 g of a thickening agent, e.g. carbomer 940, and the corresponding amount of 1N sodium hydroxide solution. 6000 g of petrolatum are mixed with 6000 g of a fatty alcohol, e.g. stearyl alcohol, with the addition of 3000 g of an emulsifier, e.g. polyoxyethylene sorbitan monolaurate. Both oil and water phase are heated separately to 70° C. and then mixed together. After homogenisation and cooling, 1000 tubes are filled with 40 g of O/W ointment each.

The following examples are intended to illustrate the invention and are not to be construed as being limitations thereon. Temperatures are given in degrees Centigrade.

EXAMPLE 1

5-Carboxy-2-(4,5-dihydro-2-thiazolyl)-pyridine

Sodium (11 mmol) is added to a flask containing 75 ml of ethanol. As soon as the sodium has dissolved, 10 mmol of 5-carboxy-2-cyanopyridine and 11 mmol of 2-amino-ethanethiol are added and the solution is refluxed for 24 h. The solution is then diluted with 25 ml of water, made acidic (pH=5) with 2N HCl and evaporated. The residue is dissolved in 100 ml of hot chloroform, the salts are filtered off and the filtrate on cooling gives crystals of the title compound, m.p. 234°–235° C.

The starting material is prepared as follows:

To a suspension of nicotinic acid N-oxide (0.7 g, 5 mmol) in 10 ml of dichloromethane is added trimethylsilylcyanide (0.55 g, 5,5 mmol), and the solution is stirred for 5 min. Then dimethylcarbamoyl chloride (0.54 g, 5 mmol) is added, and stirring is continued for 5 days under reflux. After cooling, the solution is evaporated to dryness under reduced pressure, and the residue is dissolved in 50 ml of hot water. After standing overnight, the white precipitate is filtered off and is purified by column chromatography (ethyl acetate/ethanol 1:1) to yield 5-carboxy-2-cyano-pyridine, m.p. 194°–195° C., $R_f$=0.54.

EXAMPLE 2

5-Carboxy-2-(2-thiazolyl)-pyridine

A mixture of 500 mg (2.4 mmol) of 5-carboxy-2-(4,5-dihydro-2-thiazolyl)-pyridine, 50 mg of 10% Pd on C and 5 g of diphenylether is refluxed for 4 h. The mixture is then diluted with methanol and the catalyst filtered off. The methanol is evaporated and some hexane added to the residue. The diphenylether dissolves and a solid is left, which is filtered off and washed with hexane. This residue is dissolved again in methanol and treated with charcoal. After evaporation of the methanol the title compound, m.p. >300°, is obtained.

EXAMPLE 3

2-(2-Benzothiazolyl)-5-carboxy-pyridine

Sodium (7.7 mmol) is added to a flask containing 70 ml of ethanol. As soon as the sodium has dissolved, 7 mmol of 5-carboxy-2-cyanopyridine and 8.4 mmol of 2-amino-thiophenol are added and the solution is refluxed for 24 h. The solid formed is filtered off, redissolved in ethanol and water, the solution is made acidic (pH=3) with 2N HCl and evaporated. The residue is dissolved in 100 ml of hot ethyl acetate, the salts are filtered off and the filtrate on cooling gives crystals of the title compound, m.p. >300°.

EXAMPLE 4

5-Carboxy-2-(4,5-dihydro-2-oxazolyl)-pyridine

Under a nitrogen atmosphere, sodium (12 mmol) is added to a flask containing 10 ml of anhydrous methanol. After the sodium has dissolved, a solution of 5-carboxy-2-cyano-pyridine (5 mmol) in 5 ml of methanol is added dropwise. The mixture is heated at 50° for 1.5 h. The mixture is allowed to cool and a solution of ethanolamine (10 mmol) in a mixture of 5 ml methanol and 1.5 of concentrated HCl is added dropwise. After addition is complete, the reaction mixture is refluxed for 2 h. The solvent is evaporated, the residue dissolved in 45 ml of hot ethanol, the salts are filtered off and the filtrate on cooling gives crystals of the title compound, m.p. 286°–287°.

EXAMPLE 5

5-Carboxy-2-(5-tetrazolyl)-pyridine

Sodium azide (12.0 g, 0.18 mol) and anhydrous ammonium chloride (1.5 g) are added to a stirred solution of 5-carboxy-2-cyanopyridine (22.0 g, 0.15 mol) in dry dimethylformamide (375 ml). The reaction mixture is heated to 80° and held at this temperature for 24 h. After this time, a further portion of sodium azide 6.0 g, 0.09 mol) is added and heating continued for a further 24 h. The reaction mixture is then allowed to cool to ambient temperature and diluted with water (560 ml). This solution is acidified to pH 3 with 5N hydrochloric acid and, while a solid precipitates, stirred at this pH for 30 min. The product is filtered off and stirred in refluxing water (60 ml) for 15 min. It is then refiltered, washed with dichloromethane (5×20 ml) and dried in vacuo at 60° to yield the title compound as a light solid; m.p. 257°–259°.

EXAMPLE 6

5-Carboxy-2-(4,5-dihydro-2-imidazolyl)-pyridine

A solution of sodium methoxide is prepared by careful addition of sodium metal (13.6 g, 0.59 mol) to a flask containing methanol (500 ml) which is stirred. A solution of 5-carboxy-2-cyano-pyridine (36.0 g, 0.24 mol) in methanol (200 ml) is added to the sodium methoxide and the mixture heated for 2 h at 50°. After this time, freshly distilled ethylenediamine (28.8 g, 0.48 mol) and concentrated hydrochloric acid (64 ml) is added to the solution, which is then heated to 80° for 2.5 h. The reaction mixture is evaporated in vacuo to dryness. The residue is slurried in hot water (75 ml) for 15 min, filtered, washed with cold methanol (2×25 ml) and dried in vacuo at 60° to yield the title compound; m.p. 344°–345°.

EXAMPLE 7

5-Carboxy-2-(4,5-dihydro-1-ethyl-2-imidazolyl)-pyridine Sodium (12 mmol) is added to a flask containing 20 ml of methanol. After the sodium has dissolved, a solution of 5-carboxy-2-cyanopyridine (5 mmol) in 10 ml of methanol is added dropwise. The mixture is heated at 50° for 3 h. Then, 5 mmol of 2-ethylamino-ethylamine and 1.5 ml of HCl conc. are added, and the heating is continued at 80° for 3 h. The reaction mixture is allowed to cool and the resulting precipitate is filtered off, dried and purified by silica gel column chromatography with methanol : dichloromethane: 25% aqueous ammonia (6:4:0.1) as eluant. Thus, the title compound, m.p. 254°–256°, is obtained.

EXAMPLE 8

Methyl 5-carboxy-pyridine-2-carboximidate

Sodium (12 mmol) is added to a flask containing 20 ml of methanol. After the sodium has dissolved, 5 mmol of 5-carboxy-2-cyano-pyridine is added. The mixture is heated at 50° for 6 h. After cooling, the reaction mixture is diluted with water and acidified (pH=5)with 2N HCl. The solid is collected and dried, and corresponds to the title compound, m.p. 284°–286°.

EXAMPLE 9

5-Carboxy-2-(N-ethylamidino)-pyridine hydrochloride

Sodium (12 mmol) is added to a flask containing 30 ml of methanol. After the sodium has dissolved, 5 mmol of 5-carboxy-2-cyano-pyridine is added. The mixture is heated at 50° for 6 h. Then, 10 mmol of a solution of ethylamine hydrochloride in 10 ml of methanol is added dropwise and the temperature raised to 80° for 17 h. After cooling, the solution is evaporated to dryness, the residue dissolved in 30 ml of water and the pH adjusted to 3. The solid is collected and dried and corresponds to the title compound, m.p. >290°.

EXAMPLE 10

1-(5-Carboxy-2-pyridinyl)-1-butanone

To a stirred solution of propyl magnesium bromide (67.5 mmol) in 80 ml of ether, 5-carboxy-2-cyano-pyridine (30.7 mmol), dissolved in 100 ml of tetrahydrofuran, is added dropwise. The mixture is refluxed for 20 h. After cooling, 10 ml of water and 5 ml of 5N $H_2SO_4$ are added. Extraction of the aqueous phase with ether and evaporation of the solvent yield 3.5 g of crude product. Purification by silica gel column chromatography (n-hexane: ethyl acetate: HCOOH 7:3:0.1) yields the title compound, m.p. 128°–130°.

EXAMPLE 11

1-(5-Carboxy-2-pyridinyl)-1-butanone oxime

To a stirred solution of 1-(5-carboxy-2-pyridinyl)-1-butanone (2 mmol) in 20 ml of pyridine, hydroxylamine hydrochloride (4 mmol) is added. The reaction mixture is stirred at room temperature for 5 h. The solvent is distilled off and the residue crystallized from ethyl acetate; m.p. 203°–205°.

EXAMPLE 12

5-Carboxy-pyridine-2-carboxamide oxime

Sodium (18 mmol) is added to a flask containing 20 ml of ethanol. After the sodium has dissolved, 3.8 mmol of 5-carboxy-2-cyanopyridine and 18 mmol of hydroxylamine hydrochloride are added, and the solution is refluxed for 5 h. After cooling, the resulting precipitate is filtered off and recrystallized from water; m.p. >300°.

EXAMPLE 13

5-Carboxy-2-N-hydroxycarbamoyl-pyridine

A 5N sodium hydroxide solution (300 ml) is added slowly with stirring to a mixture of hydroxylamine sulfate (49.2 g, 0.3 mol) and ice (50 g). Sodium sulfite (6.0 g) followed by 5-carboxy-2-methoxycarbonyl-pyridine [cp. e.g. C. A. 68, 688400h (1968)](54.3 g, 0.3 mol) is added and the mixture stirred at ambient temperature until a clear solution results. This solution is stirred at 45°–50° for 24 h. After cooling, the solution is acidified to pH 3 using 5N hydrochloric acid. A beige solid precipitates. This solid is filtered off and then slurried in hot water (70°–80°, 250 ml) for 15 min. The product is filtered off, washed with a little cold water (25–50 ml) and dried in vacuo at 60° to yield the title compound as a light solid; m.p. 219°–223°.

EXAMPLE 14

Isoquinoline-1,4-dicarboxylic acid

A stirred solution of 1-cyano-isoquinoline-4-carboxylic acid (1.98 g, 0.01 mol) in 15 ml of 32% aqueous NaOH is refluxed for 3 h. After cooling, the solution is acidified with 5N HCl to pH=3. The resulting precipitate is filtered off, washed with water and dried to yield the title compound, m.p. 228°–229°.

The starting material is prepared as follows:

(a) 4-Carboxy-isoquinoline [J. Amer. Chem. Soc. 67, 1268 (1945)](10 g, 0.058 mol) is refluxed in 100 ml of acetic acid containing 13 ml of hydrogen peroxide (30%) overnight. After cooling, the solution is evaporated to dryness and the residue is purified by column chromatography (ethyl acetate/methanol/formic acid 3:2:1) to yield 4-carboxy-isoquinoline N-oxide, m.p. 280°–283°, $R_f$=0.3.

(b) To a suspension of 4-carboxy-isoquinoline N-oxide (0.65 g, 3.4 mmol) in 20 ml of dichloromethane is added trimethylsilylcyanide (0.7 g, 7 mmol), and stirring is continued for 5 min. After this time, dimethylcarbamoyl chloride (0.75 g, 7 mmol) is added, and the solution is stirred for 5 days under reflux. After cooling, the reaction mixture is evaporated to dryness. The residue is dissolved in 50 ml of a hot mixture of ethanol/water and left overnight in a refrigerator. The resulting crystals are filtered off and dried, and correspond to 1-cyano-isoquinoline-4-carboxylic acid, m.p. 216°.

EXAMPLE 15

4-Carboxy-1-(5-tetrazolyl)-isoquinoline

The title compound, m.p. 292°, is prepared analogously as described in Example 5 starting from 1-cyano-isoquinoline-4-carboxylic acid instead of 5-carboxy-2-cyano-pyridine.

EXAMPLE 16

Methyl 4-carboxy-isoquinoline-1-carboxylate and dimethyl isoquinoline-1,4-dicarboxylate To a stirred solution of isoquinoline-1,4-dicarboxylic acid (4.1 g, 18.9 mmol) in 200 ml of methanol, concentrated sulfuric acid (1 ml) is added. The reaction mixture is refluxed for 15 h. After cooling, the solution is poured into 20 ml of cold water. The precipitate formed is collected, washed with cold water and purified by silica gel column chromatography (acetone-methanol-formic acid 9:1:0.1). Methyl 4-carboxy-isoquinoline-1-carboxylate (m.p. 189°, $R_f$=0.88) and dimethyl isoquinoline-1,4-dicarboxylate (m.p. 69°–70°, $R_f$=0.96) are obtained as separate fractions.

EXAMPLE 17

5-Carboxy-2-(2-imidazolyl)-pyridine

5-Carboxy-2-(4,5-dihydro-2-imidazolyl)-pyridine (0.5 g, 2.6 mmol) is dissolved in 50 ml of diphenylether, and 50 of Pd/C (10%) are added. The mixture is refluxed for 8 h, then filtered. The solid containing the charcoal and the product is dissolved in hot methanol and filtered. The methanol is evaporated to yield the title compound, m.p. >300°.

EXAMPLE 18

4-n-Butyl-5-carboxy-2-(5-tetrazolyl)-pyridine

The title compound, m.p. >300°, is prepared analogously as described in Example 5 starting from 4-n-butyl-5-carboxy-2-cyano-pyridine instead of 5-carboxy-2-cyano-pyridine.

The starting material is prepared as follows:

(a) 4-n-Butyl-pyridine-3-carboxaldehyde [cp. Heterocycles 22, 339–344 (1984)](10 g, 0.061 mol) is dissolved in tetrahydrofuran (100 ml). This solution is mixed with a cold solution of metachloroperbenzoic acid (26.3 g, 0.15 mol) in THF (200 ml), and the resulting mixture is stirred at room temperature overnight. The white precipitate is filtered, washed with THF and dried to yield 4-n-butyl-3-carboxy-pyridine N-oxide; m.p. 164°–165°.

(b) To a suspension of 4-n-butyl-3-carboxy-pyridine N-oxide (600 mg, 3 mmol) in 15 ml of dichloromethane is added trimethylsilylcyanide (595 mg, 6 mmol), and the solution is stirred for 5 min. Then dimethylcarbamoyl chloride (645 mg, 6 mmol) is added and stirring continued for 4 days under reflux. After cooling, the solution is evaporated to dryness under reduced pressure, and the residue is purified by column chromatography (dichloromethane/methanol 3:1) to yield 4-n-butyl-5-carboxy-2-cyano-pyridine, m.p. 267°–268°, $R_f=0.3$.

EXAMPLE 19

4-n-Butyl-pyridine-2,5-dicarboxylic acid

A stirred solution of 4-n-butyl-5-carboxy-2-cyano-pyridine (500 mg, 2,4 mmol) in 10 ml of aqueous NaOH (32%) is refluxed for 3 h. After cooling, the solution is acidified with 2N HCl to pH=3. The resulting precipitate is recrystallized in hot water to yield the title compound, m.p. 239°.

EXAMPLE 20

5-Carboxy-4-phenyl-2-(5-tetrazolyl)-pyridine

The title compound, m.p. >300°, is prepared analogously as described in Example 5 starting from 5-carboxy-2-cyano-4-phenylpyridine instead of 5-carboxy-2-cyano-pyridine.

The starting material is prepared as follows:

(a) Methyl 4-phenylnicotinate [cp. Heterocycles 22, 151–157 (1984)](53 g, 0.25 mol), 5N aqueous NaOH solution (100 ml) and methanol (100 ml) are refluxed together with stirring for 1 h. The reaction solution is allowed to cool, acidified with concentrated HCl to pH 4 and evaporated to dryness in vacuo. The residue is slurried in hot ethanol (75 ml), filtered, and the filtrates are evaporated to dryness in vacuo. The residue obtained is slurried in cold ethyl acetate (30 ml), filtered and dried to give 4-phenylnicotinic acid hydrochloride, m.p. 239°–241°.

(b) 4-Phenylnicotinic acid hydrochloride (2.4 g, 0.01 mol) is dissolved in water (50 ml) and the pH is adjusted to pH 10–11 by the addition of 5N aqueous NaOH solution. A solution of peracetic acid (40% w/v, 15.2 g) is added cautiously at ambient temperatures. When the addition is complete, the reaction mixture is stirred at ambient temperature for 15 min and then heated at 50° for 4 h. After this period, the mixture is allowed to cool and evaporated in vacuo to dryness. The residue is slurried in hot ethanol (20 ml), then filtered, and the filtrates are evaporated to dryness in vacuo to yield 4-phenylnicotinic acid N-oxide.

(c) To a solution of 4-phenylnicotinic acid N-oxide (8.4 g, 0.04 mol), sodium cyanide (6.45 g, 0.13 mol) and diethylamine (26.2 ml, 0.19 mol) in absolute dimethylformamide (200 ml), chlorotrimethylsilane (23.8 ml, 0.19 mol) is added. The reaction mixture is then heated for 26 h at 100°–110°. After cooling, the solution is poured into 200 ml of water and the pH is adjusted to pH 4 by the addition of concentrated HCl. The mixture is extracted with ethyl acetate and the extracts are concentrated. The dark residue is dissolved in 150 ml of ethyl acetate and extracted with a saturated solution of sodium hydrogen carbonate. This latter extract is acidified with concentrated HCl to pH 4 and extracted again with ethyl acetate. The combined ethyl acetate extracts are evaporated to dryness, and the residue is chromatographed in ethyl acetate/methanol (1:1) on Florisil ® [magnesium silicate (30–60 mesh, Fluka, Buchs, CH)]to yield 5-carboxy-2-cyano-4-phenyl-pyridine, m.p. 270°–272°, $R_f=0.6$.

EXAMPLE 21

5-Carboxy-4-cyclohexyl-2-(5-tetrazolyl)-pyridine

The title compound, m.p. 278°, is prepared analogously as described in Example 5 starting from 5-carboxy-2-cyano-4-cyclohexyl-pyridine instead of 5-carboxy-2-cyano-pyridine.

The starting material is prepared as follows:

(a) Methyl 4-cyclohexylnicotinate [cp. Heterocycles 22, 151–157 (1984)] (23.6 g, 0.11 mol), 5N aqueous NaOH solution (100 ml) and methanol (50 ml) are refluxed together with stirring for 1 h. The reaction solution is allowed to cool and acidified with concentrated hydrochloric acid to pH 4. The mixture is evaporated to dryness in vacuo. The residue is slurried in hot ethanol (50 ml), filtered and the filtrates are evaporated to dryness in vacuo. The residue is slurried in cold ethyl acetate (23 ml), filtered and dried to give 4-cyclohexylnicotinic acid hydrochloride.

(b) 4-Cyclohexylnicotinic acid hydrochloride (4.5 g, 0.018 mol) is dissolved in methylene chloride (40 ml). This solution is mixed with a cold solution of metachloroperbenzoic acid (10.82 g, 0.063 mol) in $CH_2Cl_2$ (80 ml), and the resulting mixture is stirred at room temperature overnight. The precipitate obtained is filtered and the filtrate evaporated to dryness. The residue is suspended in ether. The precipitate is filtered, washed with ether and dried to yield 3-carboxy-4-cyclohexyl-pyridine N-oxide, m.p. 168°–169°. (c) To a solution of 3-carboxy-4-cyclohexyl-pyridine N-oxide (3.09 g, 0.014 mol), sodium cyanide (2.47 g, 0.05 mol) and triethylamine (7.08 g, 0.07 mol) in absolute dimethylformamide (50 ml), chlorotrimethylsilane (7.6 g, 0.07 mol) is added. The reaction mixture is then heated for 28 h at 85°. After cooling, the inorganic salts are filtered, washed with diethyl ether, and the filtrate is evaporated at 50° in vacuo. The dark residue is purified by chromatography on Florisil ® (ethyl acetate/methanol 4:1) to yield 5-carboxy-2-cyano-4-cyclohexyl-pyridine; m.p. 225°–230°, $R_f=0.55$.

EXAMPLE 22

5-Carboxy-2-[5-(2-N-acetyl)-tetrazolyl]-pyridine

A mixture of 500 mg (2.6 mmol) of 5-carboxy-2-(5-tetrazolyl)-pyridine and 50 mg of magnesium perchlorate in 10 ml of acetic anhydride is refluxed for 1 h. After cooling, the solution is evaporated to dryness. The residue is slurried in dichloromethane, filtered and dried to yield the title compound, m.p. 305°–308°.

EXAMPLE 23

Hexadecyl 2-(5-tetrazolyl)-pyridine-5-carboxylate

A mixture of 1.65 g (8.6 mmol) of 5-carboxy-2-(5-tetrazolyl)-pyridine , 0.1 ml of concentrated sulfuric acid and 3.64 g (15 mmol) of 1-hexadecanol in 50 ml of toluene is refluxed for 48 h. The hot solution is filtered in order to eliminate the non-reacted starting material.

The filtrate on cooling yields crystals of the title compound, m.p. 139°–140°.

EXAMPLE 24

Hexadecyl 2-(2-imidazolyl)-pyridine-5-carboxylate

5-Carboxy-2-(2-imidazolyl)-pyridine (1.89 g, 0.01 mol) is refluxed in 10 ml of thionyl chloride for 2 h. The solution is evaporated to dryness and the residue dissolved in 20 ml of dichloromethane. The latter solution is added dropwise to a mixture of 1-hexadecanol (2.68 g, 0.011 mol) in 1.6 ml of pyridine. After 17 h at room temperature, the precipitate is filtered off and the filtrate evaporated to dryness. The resulting residue is crystallized in toluene to yield the title compound, m.p. 97°–98°.

EXAMPLE 25

5-Hexadecyloxycarbonyl-2-(N-hexadecyl-N-hexadecyloxycarbamoyl)-pyridine.

5-Carboxy-2-N-hydroxycarbamoyl-pyridine (1.82 g, 0.01 mol) is refluxed in 50 ml of toluene together with 1-hexadecanol (2.66 g, 0.011 mol) and 0.1 ml of conc. sulfuric acid overnight. The solution is then filtered, the filtrate is evaporated to dryness and the residue recrystallized in n-hexane/ethyl acetate to yield the title compound, m.p. 93°–95°.

EXAMPLE 26

Dihexadecyl isoquinoline-1,4-dicarboxylate

Isoquinoline-1,4-dicarboxylic acid (1.8 g, 5 mmol) is refluxed in 10 ml of thionyl chloride for 2 h. The solution is evaporated to dryness and the residue dissolved in 20 ml of dichloromethane. The latter solution is added dropwise to a mixture of 1-hexadecanol (2.90 g, 12 mmol) in 1 ml of pyridine. After 19 h at room temperature, the precipitate is filtered off and the filtrate is evaporated to dryness. The resulting residue is crystallized in toluene/ethanol. The crystals obtained are purified by silica gel flash-column chromatography (dichloromethane). Thus the title compound, m.p. 80.7°–81.4°, is obtained.

EXAMPLE 27

4-(1-ethoxycarbonyl-1-ethoxy-methoxycarbonyl)-1-{5-[2-N-(1-ethoxycarbonyl-1-ethoxy-methyl)]-tetrazolyl}-isoquinoline 4-Carboxy-1-(5-tetrazolyl)-isoquinoline (0.69 g, 2.9 mmol) is dissolved in 15 ml of dichloromethane. 1.2 ml of triethylamine and 1.8 ml (8.6 mmol) of ethyl 2-bromo-2-ethoxy-acetate is added dropwise to this solution. The reaction mixture is stirred at room temperature for 4 h. After this period, the dichloromethane solution is extracted with water, the organic layer dried over magnesium sulfate, filtered and evaporated to dryness. The residue is purified by silica gel column chromatography (dichloromethane) to yield two diastereomers of the title compound: (a): $R_f$=0.68, m.p. 97° and (b): $R_f$=0.5, /resin [IR (NaCl film): 1730 (CO), 1755 (CO) cm$^{-1}$].

EXAMPLE 28

Di(1-ethoxycarbonyl-1-ethoxy-methyl)pyridine-2,5-dicarboxylate 2,5-Dicarboxy-pyridine (1.67 g, 0.01 mol) is suspended in 40 ml of dichloromethane. 2.8 ml of triethylamine are added dropwise, followed by 4.02 g (0.02 mol) of ethyl 2-bromo-2-ethoxy-acetate. The solution is stirred at room temperature for 2 h. After this period, the dichloromethane solution is filtered, washed with water, dried over magnesium sulfate and evaporated to dryness. The residue is purified by silica gel column chromatography (dichloromethane/ethyl acetate) to yield the title compound as a resin; IR (NaCl film): 1730 (CO), 1765 (CO) cm$^{-1}$.

We claim:
1. A member selected from the group consisting of
(a) a compound of formula

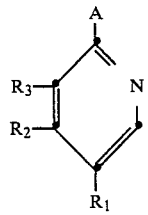

wherein
A represents 5-tetrazolyl which is unsubstituted or is substituted in the 2-position by a member selected from the group consisting of (1) $C_1$–$C_{20}$ alkyl, (2) amino-lower alkyl, (3) mono-lower alkylamino-lower alkyl, (4) di-lower alkylamino-lower alkyl, (5) carboxy-lower alkyl, (6) lower alkoxycarbonyl-lower alkyl, (7) aryl-lower alkyl, (8) hydroxy-lower alkyl, (9) lower alkanoyloxy-lower alkyl, (10) lower alkoxy-lower alkyl, (11) hydroxy-lower alkoxymethyl, (12) lower alkanoyloxy-lower alkoxymethyl, (13) lower alkoxy-lower alkoxymethyl, (14) 1-alkoxycarbonyl-1-lower alkoxymethyl, (15) 3-phthalidyl, (16) lower alkyl-3-phthalidyl, (17) lower alkoxy-3-phthalidyl, (18) halogen-3-phthalidyl, (19) lower alkoxycarbonyloxy-lower alkyl and (20) lower alkanoyl;
$R_1$ represents carboxy or a pharmaceutically acceptable ester group thereof;
$R_2$ represents hydrogen or a member selected from the group consisting of lower alkyl, cycloalkyl, aryl-lower alkyl, heteroaryl-lower alkyl and aryl each of which members can be unsubstituted or substituted; and
$R_3$ represents hydrogen;
(b) a tautomer thereof and (c) a pharmaceutically acceptable salt thereof.

2. A compound according to claim 1,
wherein
$R_2$ represents hydrogen or a member selected from the group consisting of lower alkyl, cycloalkyl, aryl-lower alkyl, heteroaryl-lower alkyl and aryl each of which members can be unsubstituted or substituted by amino, lower alkylamino, di-lower alkylamino, N-piperidino, N-morpholino, N-thiomorpholino, N-piperazino, 4-(lower alkyl or lower alkanoyl)-N-piperazino, lower alkoxy, $C_3$–$C_{14}$-alkoxy wherein the alkyl chain is interrupted by 1 to 5 oxy groups, or $C_3$–$C_{14}$-alkylamino wherein the alkyl chain is interrupted by 1 to 5 oxy and/or imino groups; and
$R_3$ represents hydrogen.

3. A compound according to claim 1,
wherein
A represents 5-tetrazolyl, 2-lower alkanoyl-5-tetrazolyl or 2-(1-lower alkoxycarbonyl-1-lower alkoxymethyl)-5-tetrazolyl;

$R_1$ represents carboxy, $C_1$–$C_{20}$-alkoxycarbonyl or 1-lower alkoxycarbonyl-1-lower alkoxy-methoxycarbonyl;

$R_2$ represents hydrogen, lower alkyl, $C_5$–$C_7$-cycloalkyl, phenyl-lower alkyl or phenyl, wherein in the latter two radicals, phenyl is unsubstituted or substituted by lower alkyl, hydroxy, lower alkoxy and/or halogen; and $R_3$ represents hydrogen; a tautomer of said compound or a pharmaceutically acceptable salt of said compound.

4. A compound according to claim 1, wherein

A represents 5-tetrazolyl, 2-lower alkanoyl-5-tetrazolyl or 2-(1-lower alkoxycarbonyl-1-lower alkoxymethyl)-5-tetrazolyl;

$R_1$ represents carboxy, $C_1$–$C_{20}$-alkoxycarbonyl or 1-lower alkoxycarbonyl-1-lower alkoxy-methoxycarbonyl;

$R_2$ represents hydrogen, lower alkyl, $C_5$–$C_7$-cycloalkyl or phenyl; and $R_3$ represents hydrogen;

a tautomer of said compound or a pharmaceutically acceptable salt of said compound.

5. A compound according to claim 1, wherein $R_2$ and $R_3$ represent hydrogen; or a pharmaceutically acceptable salt thereof.

6. A compound according to claim 1, wherein A represents 5-tetrazolyl, $R_1$ represents carboxy or lower alkoxycarbonyl, $R_2$ is hydrogen, lower alkyl, cycloalkyl, phenyl-lower alkyl or phenyl, wherein in the latter two radicals, phenyl is unsubstituted or substituted by lower alkyl, hydroxy, lower alkoxy and/or halogen, and $R_3$ represents hydrogen; a tautomer of said compound or a pharmaceutically acceptable salt of said compound.

7. A compound according to claim 1, wherein A represents 5-tetrazolyl, $R_1$ is carboxy or lower alkoxycarbonyl, $R_2$ is hydrogen or lower alkyl and $R_3$ represents hydrogen; or a pharmaceutically acceptable salt thereof.

8. A compound according to claim 1, said compound being 5-carboxy-2-(5-tetrazolyl)-pyridine.

9. A compound according to claim 1, said compound being hexadecyl 2-(5-tetrazolyl)pyridine-5-carboxylate.

10. A pharmaceutical composition comprising an amount of a compound, a tautomer or a salt according to claim 1 effective for the treatment of diseases responsive to collagen proline-4-hydroxylase inhibition in mammals together with at least one pharmaceutically acceptable carrier.

11. A method of treating diseases responsive to collagen proline-4-hydroxylase inhibition in mammals comprising the administration to a mammal in need thereof of a therapeutically effective amount of a compound, a tautomer or salt according to claim 1.

12. A method of decreasing collagen synthesis in a mammal comprising the administration to said mammal of an effective amount of a compound, a tautomer or salt according to claim 1.

* * * * *